United States Patent
Hobot et al.

(10) Patent No.: US 12,329,893 B2
(45) Date of Patent: Jun. 17, 2025

(54) SINGLE CONTAINER PREPARATION OF PERITONEAL DIALYSIS FLUID

(71) Applicant: MOZARC MEDICAL US LLC, Minneapolis, MN (US)

(72) Inventors: Christopher M Hobot, Rogers, MN (US); Thomas E Meyer, Stillwater, MN (US)

(73) Assignee: MOZARC MEDICAL US LLC, Minneapolis, MN (US)

(*) Notice: Subject to any disclaimer, the term of this patent is extended or adjusted under 35 U.S.C. 154(b) by 1059 days.

(21) Appl. No.: 17/208,251

(22) Filed: Mar. 22, 2021

(65) Prior Publication Data

US 2022/0296794 A1    Sep. 22, 2022

(51) Int. Cl.
*A61M 1/28* (2006.01)
*A61M 1/16* (2006.01)

(52) U.S. Cl.
CPC .......... *A61M 1/282* (2014.02); *A61M 1/1656* (2013.01); *A61M 1/1666* (2014.02); *A61M 1/167* (2014.02); *A61M 1/1672* (2014.02); *A61M 1/1694* (2013.01); *A61M 1/1696* (2013.01); *A61M 1/287* (2013.01); *A61M 2205/125* (2013.01)

(58) Field of Classification Search
CPC .. A61M 1/1666; A61M 1/167; A61M 1/1672; A61M 1/1696; A61M 1/282; A61M 1/287; A61M 2205/125; A61M 1/1656; A61M 1/1694
See application file for complete search history.

(56) References Cited

U.S. PATENT DOCUMENTS

| | | | |
|---|---|---|---|
| 7,544,300 B2 | 6/2009 | Burbank | |
| 7,749,393 B2 | 7/2010 | Brugger | |
| 7,976,711 B2 | 7/2011 | Brugger | |
| 8,202,420 B2 | 6/2012 | Brugger | |
| 8,460,558 B2 | 6/2013 | Brugger | |
| 8,585,634 B2 | 11/2013 | Neftel | |
| 9,155,824 B2 | 10/2015 | Eyrard | |
| 9,731,059 B2 | 8/2017 | Crnkovich | |
| 9,861,733 B2 | 1/2018 | Burbank | |
| 9,907,897 B2 | 6/2018 | Burbank | |
| 10,076,599 B2 | 9/2018 | Eyrard | |
| 2017/0281846 A1* | 10/2017 | Manda | A61K 31/19 |
| 2018/0326138 A1 | 11/2018 | Kalaskar | |
| 2023/0277739 A1* | 9/2023 | Visciano | A61M 1/1666 604/28 |

FOREIGN PATENT DOCUMENTS

| | | |
|---|---|---|
| EP | 1187642 | 3/2002 |
| EP | 1592494 | 6/2009 |
| EP | 2719406 B1 | 5/2016 |
| EP | 3016695 B1 | 5/2016 |
| EP | 2484333 | 11/2017 |
| EP | 1648536 | 12/2017 |
| EP | 1648536 B1 | 12/2017 |
| EP | 3285825 A1 | 2/2018 |
| EP | 3395382 A1 | 10/2018 |
| EP | 3903851 A1 * | 11/2021 |

* cited by examiner

Primary Examiner — John Kim (57) ABSTRACT

The invention relates to systems and methods for generation and use of peritoneal dialysis fluid. The peritoneal dialysis fluid is generated by dissolving solids or diluting concentrated liquids in a single container having all components of the final peritoneal dialysis fluid.

30 Claims, 3 Drawing Sheets

SINGLE CONTAINER PREPARATION OF PERITONEAL DIALYSIS FLUID

FIELD

The invention relates to systems and methods for generation and use of peritoneal dialysis fluid. The peritoneal dialysis fluid is generated by dissolving solids or diluting a highly concentrated liquid solution in a single container having all components of the final peritoneal dialysis fluid.

BACKGROUND

Peritoneal dialysis treatment generally requires 3-4 exchanges of peritoneal dialysis fluid per day totaling 12-15 L and can be much more in some patients. Known systems and methods use pre-mixed, sterilized peritoneal dialysis fluid and storage of these solutions puts significant burden on the patient using the fluids. Each patient typically uses a combination of three different peritoneal dialysis fluid formulations and needs to have all three on-hand in case they are needed. Because supplies are typically delivered monthly, traditional peritoneal dialysis systems require storage for upwards of 900-1,000 L of sterile fluid. Further, the patient or caregiver must move and manipulate large and cumbersome dialysate containers multiple times each day. Finally, because the pre-mixed fluids can freeze in cold weather, special accommodations must be made to receive and store fluids to protect them from freezing in cold climates. This places additional burden on patients that live in cold climates.

As such, there is a need for systems and methods that reduce the storage requirements by reconstituting peritoneal dialysis fluid from solid material or a highly concentrated liquid solution. The need extends to systems and methods that use a single container for peritoneal dialysis fluid generation rather than multiple concentrate sources.

SUMMARY OF THE INVENTION

The problem to be solved by the present invention is preparation of peritoneal dialysis fluid with minimal complexity and storage requirements. The solution is to use a single container having all components of the peritoneal dialysis fluid in solid or highly concentrated liquid form for reconstitution.

The first aspect of the invention relates to a system. In any embodiment, the system can include a water source; a dialysate container; the dialysate container initially containing solid material or a concentrated liquid; and a control system programmed to pump a predetermined volume or predetermined mass of water into the dialysate container to generate a peritoneal dialysis fluid.

In any embodiment, the system can include a water purification module between the water source and the dialysate container.

In any embodiment, an inlet of the dialysate container can include a mixing element in the dialysate container.

In any embodiment, the mixing element can be a venturi tube in an inlet of the dialysate container.

In any embodiment, the venturi tube can include a first section distal to an interior portion of the dialysate container, the first section having a first diameter; a second section distal to the first section and proximal to the interior portion of the dialysate container, the second section having a second diameter smaller than the first diameter forming a constriction, and a third section distal to the second section and extending inwardly into the interior portion of the dialysate container, the third section having a third diameter larger than the second diameter, and having a suction port exposing an interior of the venturi tube to the interior portion of the dialysate container.

In any embodiment, the system can include a cycler fluidly connectable to the dialysate container.

In any embodiment, the control system can be further programmed to pump a predetermined volume of the peritoneal dialysis fluid into the cycler.

In any embodiment, the system can include a sterilization module between the dialysate container and the cycler.

In any embodiment, the solid material or concentrated liquid can include sodium chloride, calcium chloride, magnesium chloride, sodium lactate, sodium bicarbonate, and an osmotic agent.

In any embodiment, the osmotic agent can be dextrose.

In any embodiment, the water purification module can include one or more selected from the group of a sorbent cartridge, activated carbona reverse osmosis module, an electrodialysis module, a carbon filter, and a nanofilter.

In any embodiment, the water source can be a tap water source.

In any embodiment, the water source can be a purified water source.

In any embodiment, the system can include a recirculation line, the recirculation line having an inlet and outlet fluidly connected to the dialysate container.

In any embodiment, the dialysate container can initially contain a solid material.

In any embodiment, the system can include at least one sensor in communication with the control system, the control system determining a concentration of at least one solute in the peritoneal dialysis fluid based on data from the at least one sensor.

In any embodiment, the system can include a heater between the water source and the dialysate container.

In any embodiment, the system can include a heater in the recirculation line.

The features disclosed as being part of the first aspect of the invention can be in the first aspect of the invention, either alone or in combination, or follow any arrangement or permutation of any one or more of the described elements. Similarly, any features disclosed as being part of the first aspect of the invention can be in a second aspect of the invention described below, either alone or in combination, or follow any arrangement or permutation of any one or more of the described elements.

The second aspect of the invention relates to a method. In any embodiment, the method can include the steps of pumping a predetermined volume or predetermined mass of water from a water source into a dialysate container to generate a peritoneal dialysis fluid; the dialysate container initially containing solid material or a concentrated liquid.

In any embodiment, the method can include the step of recirculating fluid through the peritoneal dialysate container.

In any embodiment, the method can include the step of heating the fluid while recirculating the fluid through the dialysate container.

In any embodiment, the water purification module can include one or more selected from the group of a sorbent cartridge, activated carbon, a reverse osmosis module, an electrodialysis module, a carbon filter, and a nanofilter.

In any embodiment, the solid material or concentrated liquid can include sodium chloride, calcium chloride, magnesium chloride, sodium lactate, sodium bicarbonate, and an osmotic agent.

In any embodiment, the osmotic agent can be dextrose.

In any embodiment, the method can include the step of infusing the peritoneal dialysis fluid into a patient.

In any embodiment, an inlet of the dialysate container can have a mixing element.

In any embodiment, the mixing element can be a venturi tube.

In any embodiment, the venturi tube can include a first section distal to an interior portion of the dialysate container, the first section having a first diameter, a second section distal to the first section and proximal to the interior portion of the dialysate container, the second section having a second diameter smaller than the first diameter forming a constriction, and a third section distal to the second section and extending inwardly into the interior portion of the dialysate container, the third section having a third diameter larger than the second diameter, and having a suction port exposing an interior of the venturi tube to the interior portion of the dialysate container.

In any embodiment, the method can be performed by the system of the first aspect of the invention.

The features disclosed as being part of the second aspect of the invention can be in the second aspect of the invention, either alone or in combination, or follow any arrangement or permutation of any one or more of the described elements. Similarly, any features disclosed as being part of the second aspect of the invention can be in the first aspect of the invention, either alone or in combination, or follow any arrangement or permutation of any one or more of the described elements.

DETAILED DESCRIPTION

Unless defined otherwise, all technical and scientific terms used have the same meaning as commonly understood by one of ordinary skill in the art.

The articles "a" and "an" are used to refer to one to over one (i.e., to at least one) of the grammatical object of the article. For example, "an element" means one element or over one element.

"Activated carbon" refers to a form of carbon processed to have small pores, increasing the surface area available for adsorption.

"Calcium chloride" refers to $CaCl_2$, either in solution or solid form.

A "carbon filter" can be bed of activated carbon or a fused block of carbon particles or granules that water can permeate.

The terms "communication" and "communicating" refer to an electronic or wireless link between two components.

The term "comprising" includes, but is not limited to, whatever follows the word "comprising." Use of the term indicates the listed elements are required or mandatory but that other elements are optional and may be present.

A "concentrated liquid" is a solution having a concentration of one or more solutes greater than that to be used in therapy.

The term "concentration" refers to an amount of a solute dissolved in a given amount of a solvent.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts, or features that do not affect the basic operation of the apparatus, structure or method described.

The term "constriction" refers to any portion of a feature that is reduced in size, in reference to a compared feature such as for a tube, pipe, or flow path. For example, the constriction can have a smaller diameter relative in reference to a rounded tube or pipe. The constriction can mean any smaller opening relative to a section to which the constriction is being compared to, and is not limited to any specific relative size or shape. For example, a constriction can be flattened tube that has a smaller cross-sectional area of the flow path as compared to an adjoining tubular pipe that has a larger cross-sectional area of the flow path.

The term "containing" or to "contain" refers to a substance that is within a component or container.

A "control system" can be a combination of components that act together to maintain a system to a desired set of performance specifications. The control system can use processors, memory and computer components configured to interoperate to maintain the desired performance specifications. The control system can receive data from sensors to determine a state of a system and control one or more components to maintain a desired performance specification. The control system can also include fluid or gas control components, and solute control components as known within the art to maintain performance specifications.

A "cycler" is a component or set of components for movement of fluid into and out of the peritoneal cavity of a patient.

The terms "determining" and "determine" refer to ascertaining a particular state of a system or variable(s).

The term "dextrose" refers to a simple sugar compound with a chemical formula $C_6H_{12}O_6$. Dextrose is the dextrorotatory form of glucose, and in certain embodiments, the terms dextrose and glucose can be used interchangeably.

The term "diameter" refers to a distance from one side of a circle to an opposite side of the circle through the center of the circle.

The term "dialysate container" refers to any type of container that can hold solid material or a concentrated solution to be dissolved to generate a peritoneal dialysis fluid.

The term "distal" refers to a section or component positioned away from a point of attachment or origin.

An "electrodialysis module" is a set of components that move ions through one or more semi-permeable membranes by application of an electric potential difference.

The term "exposing" in context of a suction port means allowing either side of the suction port having access to the other side of the opening or suction port.

The terms "extend inwardly" or "extending inwardly" refer to a portion of a component directed or situated in a specified direction or orientation into the interior of a component.

The terms "first," "second," and "third," and the like, refer to separate and distinct features. For example, one or more sections can be identified as a 'first section," "second section," and "third section." Alternatively, one or more diameters can be identified as a 'first diameter," "second diameter," and "third diameter."

The term "fluidly connectable" refers to the ability of providing for the passage of fluid, gas, or combination thereof, from one point to another point. The ability of providing such passage can be any connection, fastening, or forming between two points to permit the flow of fluid, gas, or combinations thereof. The two points can be within or between any one or more of compartments of any type, modules, systems, components, and rechargers.

The term "fluidly connected" refers to a particular state such that the passage of fluid, gas, or combination thereof, is provided from one point to another point. The connection state can also include an unconnected state, such that the two points are disconnected from each other to discontinue flow. It will be further understood that the two "fluidly connectable" points, as defined above, can from a "fluidly connected" state. The two points can be within or between any one or more of compartments, modules, systems, components, and rechargers, all of any type.

The terms "forming," "forms," and the like refers to any type of shape or structure of an object or feature.

The terms "generate," "generating," "is generated," and the like refer to forming a solution or substance from constituent parts.

A "heater" is a component that is used to raise the temperature of container or substance.

The terms "heating" or to "heat" refer to a process of raising a temperature of a substance or container.

The terms "infusing" or to "infuse" refer to the movement of peritoneal dialysis fluid into a body cavity or part of a patient such as a peritoneal cavity.

The term "initially" refers to a state of a component or system prior to a process.

The term "inlet" can refer to a portion of container, flow path, or component through which fluid, gas, or a combination thereof can be drawn into the container, flow path, or component.

The term "interior" or interior portion" refers to an area inside of a given component or system.

"Magnesium chloride" refers to $MgCl_2$, either in solution or solid form.

The term "mixing element" refers to one or more components that cause turbulence in fluids, enhancing mixing.

A "nanofilter" is a filter membrane having nanometer sized pores.

An "osmotic agent" is a substance dissolved in water capable of driving a net movement of water by osmosis across a semi-permeable membrane due to concentration differences of the osmotic agent on each side of the semipermeable membrane.

The term "outlet" can refer to a portion of container, flow path, or component through which fluid, gas, or a combination thereof can be drawn out of the container, flow path, or component.

"Peritoneal dialysis fluid" is a dialysis solution to be used in peritoneal dialysis having specified parameters for purity and sterility. Peritoneal dialysis fluid is not the same as dialysate fluid of the type used in hemodialysis.

"Peritoneal dialysis" is a therapy wherein a peritoneal dialysis fluid is infused into the peritoneal cavity, which serves as a natural dialyzer. In general, waste components diffuse from a patient's bloodstream across a peritoneal membrane into the dialysis solution via a concentration gradient. In general, excess fluid in the form of plasma water flows from a patient's bloodstream across a peritoneal membrane into the dialysis solution via an osmotic gradient.

Once the infused peritoneal dialysis solution has captured sufficient amounts of the waste components the fluid is removed. This cycle can be repeated for several cycles each day or as needed.

The term "predetermined mass" refers to an amount of a fluid or substance determined prior to a process.

The term "predetermined volume" refers to an amount of fluid determined prior to a process.

The term "programmed," when referring to a processor, can mean a series of instructions that cause a processor to perform certain steps.

The term "proximal" refers to a section or component positioned nearest or adjacent to a point of attachment or origin.

The term "pump" refers to any device that causes the movement of fluids or gases by applying suction or pressure.

The terms "pumping," "pumped," or to "pump" refer to moving or flowing a fluid using a pump of any type known to those of ordinary skill in the art.

The term "purified water source" refers to a source of water that meets applicable standards for use in peritoneal dialysis.

The terms "recirculating" or to "recirculate" refer to the movement of a fluid from a point or component and back to the point or component.

A "recirculation line" refers to a fluid line with an inlet and outlet fluidly connected to a specified point or component. The recirculation line allows fluid to travel for the specified point or component, through the recirculation line, and back to the point or component.

A "reverse osmosis module" is a set of components to drive fluid through one or more semipermeable membranes, wherein pressure is used to move the fluid from a side of the semipermeable membrane with a higher concentration of one or more solutes to a side of the semipermeable membrane with a lower concentration of the one or more solutes.

A "sensor" is a component capable of determining one or more states of one or more variables in a system.

"Sodium bicarbonate" refers to $NaHCO_3$, either in solution or solid form.

"Sodium chloride" refers to NaCl, either in solution or solid form.

"Sodium lactate" refers to $C_3H_5NaO_3$, either in solution or solid form.

The term "solid material" refers to a material in the solid phase of matter, and can include crystalline, powdered, or any other form of solid material.

A "solute" is a substance dissolved in, or intended to be dissolved in, a solvent.

The term "sorbent cartridge" refers to a cartridge containing one or more sorbent materials for removing specific solutes from solution. The term "sorbent cartridge" does not require the contents in the cartridge be sorbent based, and the contents of the sorbent cartridge can be any contents capable of removing solutes from a dialysate. The sorbent cartridge may include any suitable amount of one or more sorbent materials. In certain instances, the term "sorbent cartridge" refers to a cartridge which includes one or more sorbent materials besides one or more other materials capable of removing solutes from dialysate. "Sorbent cartridge" can include configurations where at least some materials in the cartridge do not act by mechanisms of adsorption or absorption.

The term "sterilization module" can be a component that sterilizes fluid by any process including filtration, irradiation, or any other known methods known to those of skill in the art.

The term "suction port" refers to an aperture or opening in a component or feature, commonly a tube or flow path, through which any material, fluid, gas, or combinations thereof can flow. Generally, flow is directed inwards through the suction port using any motive force such as a low pressure zone. However, the suction port is not constrained to inwardly directed flow wherein material, gas, or combinations thereof can flow outwards from the suction port under certain conditions.

A "tap water source" is a water source from which potable water can be obtained, such as a home faucet or tap. In certain embodiments, a tap water source can be a source of water that meets applicable standards for drinking water set by agencies including the WHO, EPA, and EU.

The term "venturi" as used in a "venturi tube," "venturi tube," "venturi effect," "venturi system," and the like, generally refer to a reduction in fluid pressure that results when a fluid flows through a constricted section of a flow path such as a tube.

The term "water purification module" refers to a component or components capable of removing biological and/or chemical contaminants from water.

The term "water source" refers to any source from which potable or non-potable water can be obtained.

Single Container Preparation of Peritoneal Dialysis Fluid

Figure 1:
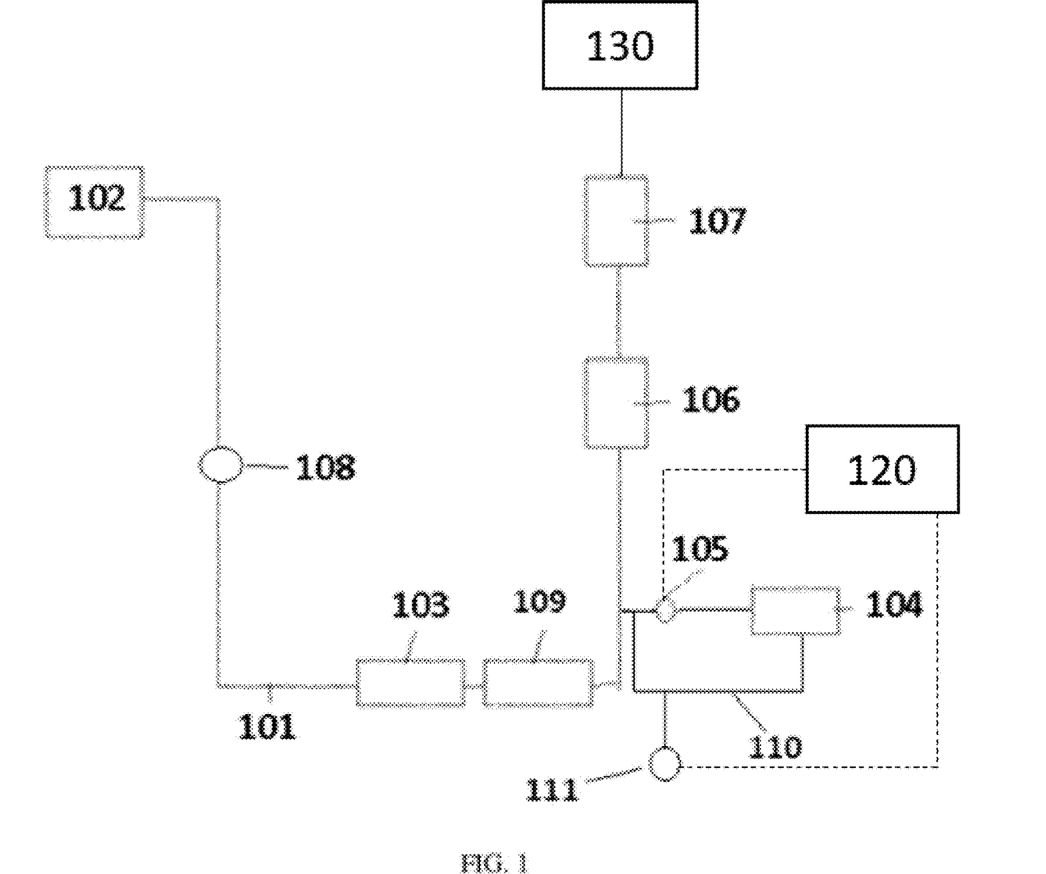
FIG. 1 is a system for generating peritoneal dialysis fluid from a single container.

FIG. 1 illustrates a system for generating peritoneal dialysis fluid from a single dialysate container 104. Water from a water source 102 can be pumped through fluid line 101 and one or more water purification modules 103 by pump 108. Water source 102 can be a potable or non-potable water source. In certain embodiments, water source 102 can be a tap water source, such as a home tap or faucet. Preferably, the water from the water source 102 will meet the WHO, EPA, and EU standards for drinking water. Water purification module 103 can remove chemical contaminants from the source water, converting the water from the water source 102 into water for injection that meets applicable pharmacopoeia requirements for peritoneal dialysis fluid.

In certain embodiments, the water purification module 103 can be a sorbent cartridge. The sorbent cartridge can include an anion exchange material, a cation exchange material, and one or more activated carbon layers or blocks. The anion exchange material can remove anionic species from the fluid, such as nitrate, phosphate, or fluoride molecules, replacing the anionic species with acetate or hydroxide ions. The sorbent cartridge can have any anion exchange material known in the art capable of removing anionic species from the fluid. Alternatively, the water purification module 103 can be a combination of cation and anion exchange materials. The sorbent cartridge can also include a cation exchange material that can remove cationic species from the fluid, such as potassium, calcium, magnesium, iron, or other cations, replacing the cationic species with hydrogen or sodium. The sorbent cartridge can include any cation exchange material capable of removing cations from the fluid. The ion exchange layer can include at least one layer or cartridge that contains a mixed bed having both cation and anion exchange materials. A mixed bed having both cation and anion exchange materials generates hydrogen ions and hydroxyl ions as byproducts that form water. Alternatively, the water purification module 103 can include cation and anion exchange resins that are not disposed in a sorbent cartridge, but are in any other type of container or conduit. The sorbent cartridge can also include activated carbon. The activated carbon operates to adsorb non-ionic molecules, organic molecules, chlorine, chloramine, and some soluble ions from the water, along with some endotoxins or bacterial contaminants. The activated carbon can be present in the sorbent cartridge in the form of a carbon block, or as a free-flowing, granular or powder layer in the sorbent cartridge. In any embodiment, the sorbent cartridge can include aluminum oxide for removal of fluoride and heavy metals. The sorbent cartridge can be sized depending on the needs of the user, ranging from a disposable unit that is replaced daily to a larger sized sorbent cartridge allowing for production of more PD fluid before the sorbent cartridge must be replaced. The water purification module 103 can alternatively or additionally include a reverse osmosis module, an electrodialysis module, one or more nanofilters, or any other system capable of removing chemical contaminants from the source water. The water purification module 103 can additionally include a microbial filter and/or a particulate filter. A microbial filter can reduce the amount of endotoxins or bacterial contaminants present in the water from water source 102. Unlike hemodialysis, peritoneal dialysis should be sterile, and the filters produce sterile fluid with low endotoxin levels that meet pharmacopoeia requirements. A particulate filter can remove particulate matter from the water.

Upon passing through water purification module 103, fluid can be optionally heated using heater 109 and pumped to a dialysate container 104 containing necessary components for carrying out peritoneal dialysis. The dialysate container 104 can initially contain solid material or a highly concentrated liquid solution. Purified water can be pumped into the dialysate container 104 to dissolve the solid material or dilute the concentrated liquid solution. In certain embodiments, pump 105 can control the movement of water into dialysate container 104 and the movement of generated peritoneal dialysis fluid out of dialysate container 104. Alternatively, or additionally, one or more valves can be included to control the movement of fluid through the system. A control system 120 can control the pumps and valves of the system to generate the peritoneal dialysis fluid. All of the components necessary for peritoneal dialysis fluid can be initially contained in dialysate container 104. For example, the dialysate container 104 can contain sodium chloride, calcium chloride, magnesium chloride, sodium lactate, sodium bicarbonate, and an osmotic agent. In certain embodiments, the osmotic agent can be dextrose or glucose. Alternatively, the osmotic agent can be icodextrin or any other material to be used as an osmotic agent in peritoneal dialysis therapy.

The control system 120 can pump a predetermined volume of water into dialysate container 104 to generate the peritoneal dialysis fluid. A flow sensor (not shown) can be used to determine the volume of water pumped into the dialysate container 104. Alternatively, scales can be used to determine a mass of water pumped into the dialysate container 104, and the control system 120 can be programmed to pump a predetermined mass of water into the dialysate container 104. In certain embodiments, one or more sensors 111 can be used to ensure that the final solute concentration of the peritoneal dialysis fluid is within a predetermined range. For example, a conductivity sensor can be used to determine the concentration of ionic components of the peritoneal dialysis fluid. Alternatively, or additionally, a refractive index sensor or other sensor can be used to determine the osmotic agent concentration in the peritoneal dialysis fluid. The sensor 111 can also be used to confirm that dissolution of the solid material is complete. When the sensor 111 provides a stable reading, the dissolution can be determined completed. The system can measure the variability of the readings from the sensor 111, and determine that dissolution is complete when the value of the reading is not fluctuating greater than a predetermined amount. Although shown in recirculation loop 110, the sensor 111 or an additional sensor can be placed in fluid line 101. The system can use the sensor 111 to ensure the incoming water from water source is within predetermined limits of one or more solutes for use in generating the peritoneal dialysis fluid.

The volume or mass of water pumped into dialysate container 104 depends on the amount of each substance initially contained within dialysate container 104. Table 1 provides non-limiting examples of the amount of each substance that can initially be placed in dialysate container 104 to which 6 L of water can be added to generate standard peritoneal dialysis fluid. Because dialysate container 104 contains all of the material that needs to be dissolved to generate a peritoneal dialysis fluid, there is no need for mixing of separate concentrates in the system.

TABLE 1

| Component | Mass |
| --- | --- |
| NaCl | 32 g |
| $CaCl_2$ | 1.5 g |
| $MgCl_2$ | 0.3 g |
| Sodium Lactate | 10-27 g |
| Sodium bicarbonate | 0-13 g |
| Dextrose | 90-255 g |
| Total | 151-325 g |

As illustrated in Table 1, when a 6 L dialysate container is used, the total weight of the constituent parts of the final peritoneal dialysis system can be 325 g or less, improving the ease of use of the system compared to 6 kg or more for the pre-mixed fluid bag. The volume of storage for a flexible 6 L container containing dry materials can be 300-500 cubic centimeters, whereas the pre-mixed fluid bag will be 6000 cubic centimeters. The smaller size necessary significantly reduces the space required to store supplies for PD treatment.

Once the peritoneal dialysis fluid is generated in dialysate container 104, the peritoneal dialysis fluid can be pumped out of dialysate container 104 and through a sterilization module 106. The sterilization module 106 can be any component or set of components capable of sterilizing the peritoneal dialysate. In certain embodiments, the sterilization module can include one or more ultrafilters. Additionally, or alternatively, a UV light source or microbial filter can be included in the sterilization module 106. The sterilization module can also include a microbial filter. Any of the components used in the sterilization module can be replaced as necessary. In certain embodiments, the sterilization module 106 can use heat sterilization. The sterilization module 106 can include a heater to heat the generated peritoneal dialysis fluid. Alternatively, or additionally, the sterilization module 106 can include a flash pasteurization module to sterilize the dialysate through flash pasteurization. The sterilization module 106 can include both heat-based sterilization components and filtration-based sterilization components, with the user adjusting the mode of sterilization based on the mode of use. For example, a heat-based sterilization can be used when the peritoneal dialysate is generated for later use, while a filtration-based sterilization can be used when the peritoneal dialysate is generated for immediate use.

After sterilization of the generated peritoneal dialysis fluid by sterilization module 106, the peritoneal dialysis fluid can be pumped to a peritoneal dialysis fluid container 107 for storage until ready for use by a patient. The peritoneal dialysis fluid container 107 can include one or more sterilized dialysate bags. The dialysate bags, once filled with peritoneal dialysate, can be stored until needed by the patient. The filled peritoneal dialysis fluid container 107 can be removed from the system and connected to a catheter or a non-integrated cycler for infusion of the peritoneal dialysate into a patient. The dialysate container can alternatively be a reusable sterilized container or bag. The reusable container or bag can be cleaned and sterilized daily, or at set time periods. Alternatively, the peritoneal dialysis fluid container 107 can be any type of storage container, such as a stainless-steel container. The connectors to the peritoneal dialysis fluid container 107 can be any type of connector known in the art. Alternatively, the dialysate container 104 can store the peritoneal dialysis fluid until used by the patient.

In certain embodiments, the system can be connected to a cycler (130) for immediate or later infusion of the generated peritoneal dialysis fluid into a patient. The peritoneal dialysis fluid can be directly infused into the patient after sterilization by connecting fluid line 101 to a catheter. Alternatively, the fluid can be stored in a peritoneal dialysis fluid container 107 and later pumped out of the peritoneal dialysis fluid container 107 and infused into the patient. Although shown as connected to fluid line 101 by a second line and pump 105, in certain embodiments dialysate container 104 can be placed in-line. That is, dialysate container 104 can be directed connected to fluid line 101.

Optionally, a heater 109 can be included upstream of dialysate container 104. The optional heater 109 can be used to facilitate dissolution of the solid PD fluid components in dialysate container 104 and maintain the peritoneal dialysis fluid near body temperature, making delivery of the peritoneal dialysis fluid to the patient more comfortable. In certain embodiments, a recirculation line 110 can be included to recirculate fluid through dialysate container 104 to ensure that the material in dialysate container 104 is fully dissolved. Although illustrated as positioned in fluid line 101 in FIG. 1, the optional heater 109 can alternatively be positioned in recirculation line 110.

The dialysate container that initially contains solid material or highly concentrated liquid for generation of the peritoneal dialysis fluid can be any type of fluid known in the art. In certain embodiments the dialysate container can be a rigid container of fixed volume. The system can optionally contain a pressure sensor that can detect when the container is filled and consequently the proper volume of fluid to prepare PD fluid has been added. In certain embodiments, the dialysate container can be a flexible and semi-compliant design that minimizes the volume required for storage prior to use. In certain embodiments, the dialysate container can include one or more components to increase the rate of dissolution of the solid material. The dialysate container can include stir bars or be placed on an external mixing apparatus.

Figure 2:
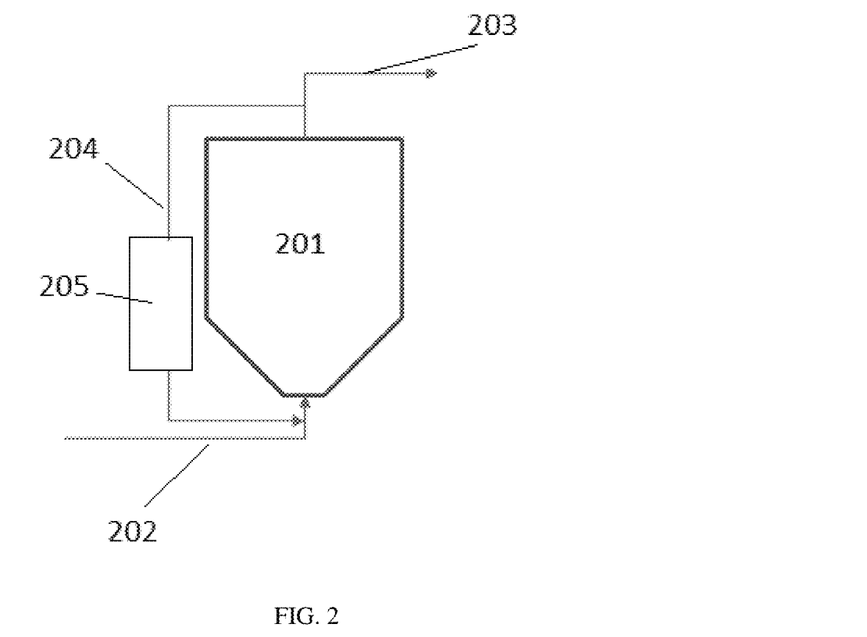
FIG. 2 is a flow diagram for a dialysate container in which peritoneal dialysis fluid can be generated.

FIG. 2 is a flow diagram using a dialysate container 201. A first fluid line 202, fluidly connected to a water source and a water purification module (not shown), can be fluidly connected to an inlet of dialysate container 201. In certain embodiments, fluid line 202 can be fluidly connected to a purified water source, and the water purification module can be omitted. Water can be pumped into dialysate container 201 to dissolve solid material or dilute a concentrated solution placed inside the dialysate container 201, generating a peritoneal dialysis fluid. The generated peritoneal dialysis fluid can be pumped out of dialysate container 201 through fluid line 203 for sterilization and use. As described, in certain embodiments, a sterilization module can be upstream of dialysate container 201, and the generated peritoneal dialysis fluid can be used without further sterilization.

In certain embodiments, a recirculation line 204 can be included, optionally with a pump (not shown). Recirculation line 204 allows fluid from an outlet of dialysate container 201 to be recirculated bac to the inlet of dialysate container 201. Recirculation of the fluid can ensure complete dissolution of the solid material in dialysate container 201. Optionally, a heater 205 can be included in the recirculation line 204. Heating the fluid can facilitate dissolution of the material in dialysate container 201. The heater can also maintain the fluid temperature near body temperature, making delivery of the peritoneal dialysis fluid to the patient more comfortable. Although shown as positioned in recirculation line 204, the optional heater 205 can also be positioned in the first fluid line 202.

Although FIG. 2 illustrates fluid line 202 connected to a bottom of dialysate container 201 and fluid line 203 connected to a top of dialysate container 201, in certain embodiments a single connector can be used as both an inlet and an outlet. The system can also include one or more pumps and/or one or more valves to control fluid movement through the fluid lines and into and out of dialysate container 201. A programmable control system (not shown) can be programmed to control the pumps and valves to add a predetermined volume of water into dialysate container 201 to generate a peritoneal dialysis fluid having specified concentrations of each solute.

Figure 3A:
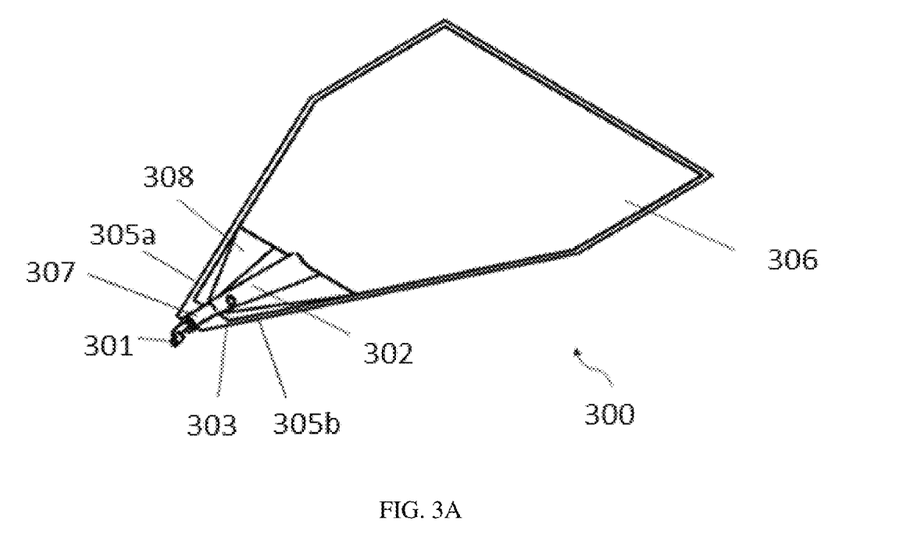
FIGS. 3A-B illustrate a non-limiting embodiment of a dialysate container.
Figure 3B:
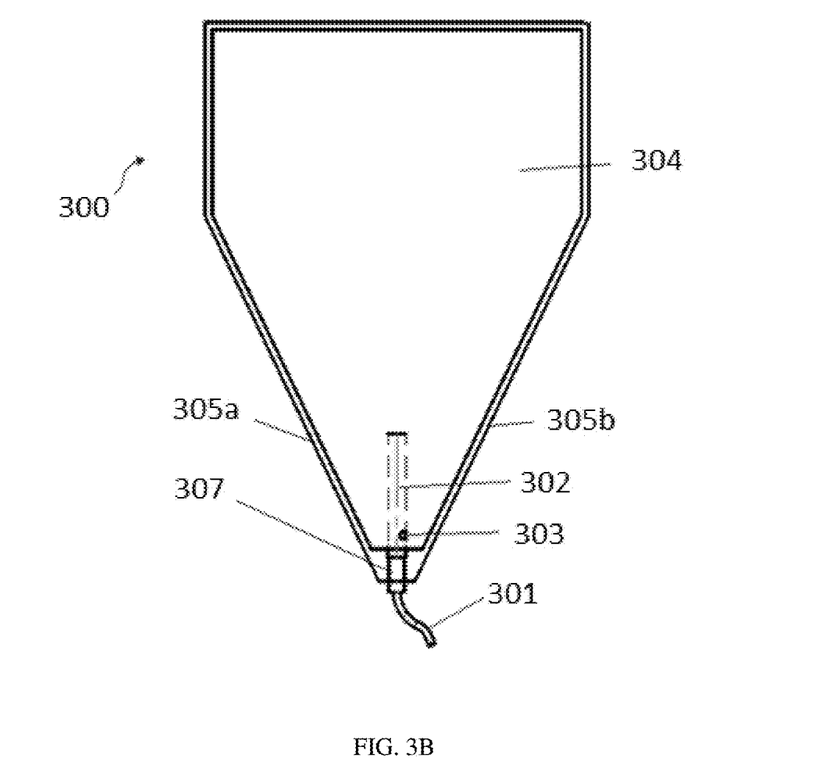

FIGS. 3A-B illustrate a non-limiting embodiment of a dialysate container 300 with a venturi tube system acting as a mixing element for easier and quicker dissolution of solid material. FIG. 3A is a perspective cut-away of an interior side 306 of a dialysate container 300. The dialysate container 300 can initially contain solid materials. Water can be pumped into the dialysate container 300 through fluid tube 302, which can be fluidly connectable to a fluid line 301. The fluid inlet tube 302 illustrated in FIG. 3A is a venturi tube. The fluid line 301 can connect to a peritoneal dialysis fluid generation system (not shown) for generation of peritoneal dialysis fluid from the solid material in dialysate container 300. The fluid tube 302 can extend inwardly into the dialysate container 300 and can include an integrated venturi feature of any type or configuration to induce a low-pressure zone after a constriction in the venturi. The low-pressure zone can be used to draw up material to dissolve solid material and form a solution within the interior portion of dialysate container 300.

The integrated venturi feature or system of the invention can have at least one suction port 303 in fluid tube 302, as well as a constriction 307 in fluid tube 302 to create a low-pressure zone due to the venturi effect. The constriction 307 inside the venturi system of fluid tube 302 increases flow velocity and reduces pressure after the constriction 307. As fluid flow exits the constriction 307, a low pressure zone is created by the pressure drop as the fluid expands in a downstream section of fluid tube 302. The reduced pressure after the constriction 307 creates a low pressure zone such that material adjacent to a suction hole 303 is drawn into the fluid tube 302. The suction port 303 can be positioned at or about a floor of the interior of the dialysate container 300 to expose an interior of the fluid tube 302 to the interior of the dialysate container 300. The suction created by the venturi effect can draws in any material such as dry powder into suction port 303. The low pressure zone at suction port 303 can draw in any dry powder into the primary flow along the fluid tube 302. At the end of the fluid tube 302, a mixture of liquid and concentrated solution can appear without any separate mechanical agitation. The suction port 303 can be downstream of the constriction 307 at any suitable position on fluid tube 302. Additional suction ports anywhere from one or more suctions ports can be included in fluid tube 302. In one embodiment, up to six or more suction ports can be used. The suction ports can be exposed to an interior space inside the dialysate container 300. As such, material inside dialysate container 300 can be drawn in through the suction port 303 positioned in the low-pressure zone after the constriction 307 in the venturi. The fluid tube 302 can have a constant outer diameter while having diameters of varying size inside the venturi system of the fluid tube 302. The material can then travel upwardly for any length of the fluid tube 302 along with any fluid being flowed into the dialysate container 300. The combined fluid/material mixture can exit at a top of the fluid tube 302 inside the dialysate container 300.

FIG. 3B is a side view of an exterior side 304 of the dialysate container 300. The fluid tube 302 can be positioned at or near a bottom portion of the dialysate container 300 in an upright position. The fluid tube 302 enters the interior of the dialysate container 300 at the bottom portion of the concentrate pouch 300. The fluid tube 302 can have a first section distal to the interior portion of the concentrate pouch 300 such that fluid flowing through the fluid tube 302 encounters the first section with a first diameter. Fluid can then flow into a second section defining the constriction 307 having a smaller diameter than the first section, forming the constriction 307. Fluid can then flow into a third section having a third diameter larger than the second section. The first diameter can be larger than the constriction 307 in the second section or the diameter in the third section. Similarly, the dimeter of the third section can be larger than one or both of the first and second section. The static pressure in the first section of the fluid tube 302 can be higher than at the second section downstream of the first section wherein any fluid speed in the first section is lower than in the second section due to a greater diameter in the first section relative to the second section.

The second section defining the constriction 307 can be proximal to the interior portion of the dialysate container 300 with respect to a third section of the fluid tube 302. The constriction 307 induces a higher fluid velocity but lower pressure. The diameter of the constriction 307 in the venturi system of the second section can be any suitable diameter relative to the first diameter sufficient to create a desired venturi effect or low pressure zone force in the third section. The third section of fluid tube 302 is distal to the second section and extends inwardly into the dialysate container 300 for any length. In one embodiment, the fluid tube 302 can extend to a top of the dialysate container 300. In another embodiment, the fluid tube 302 terminates at or near the suction port 303. As fluid exits the second section, a pressure drop is created in the third section and creates a low pressure zone that can suck up material adjacent to suction port 303. The third section has a third diameter larger than the constriction 307. The third section can create a turbulent flow and contain internal ridges or screw features (not shown) positioned along the length of an interior side of the fluid tube 302 to encourage mixture of materials suctioned into the fluid tube 302. By drawing material through the suction port 303 positioned at or near the bottom portion of the dialysate container 300, the materials can be mixed in the flowing fluid and more quickly dissolved. The mixture can then exit directly from the fluid tube 302 inside the dialysate container 300. The fluid/material mixture can then be flowed back through the suction port 303. Alternatively, the flow can reverse and mixed fluid, material, and/or solution can exit in the reverse direction through fluid tube 302. One or more pumps can reverse to provide the necessary motive force to draw the concentrate solution back through fluid tube 302.

The fluid tube 302 can extend any distance into the dialysate container 300. In certain embodiments, the fluid tube 302 can extend to a maximum of 10 mm into dialysate container 300. However, the fluid tube 302 can extend farther or shorter into the dialysate container 300, including distances greater than 10 mm. Dissolution can be unaffected over a range of sizes. As disclosed herein, any number of suction ports can be positioned in the low-pressure region to draw in material into the flow path inside fluid tube 302. In certain embodiments, the inner walls of the container body can include an inclination 305a and/or inclination 305b. In general, inclination 305a and inclination 305b can be an inwardly tapering of the inner walls of the dialysate container 300 towards the fluid tube 302 at the bottom portion of the dialysate container 300. The inclination 305a and inclination 305b can act to collect all materials including sold material, powders, partially dissolved concentrate, and/or fully dissolved concentrate at the bottom of the dialysate container 300. The collected materials and or solutions can be sucked through suction port 303 and dissolved or further mixed. Further, the inclination 305a and inclination 305b can help to avoid the creation of no-flow zones within the concentrate dialysate container 300. In certain embodiments, the inclination 305a and 305b of the inner walls can be between 20°-60°. In other embodiments, the bottom portion can be formed into a funnel to direct materials towards the suction port 303. Vertical ribs positioned on the interior side of the funnel can encourage materials and solutions to flow towards the bottom of the dialysate container 300.

The fluid tube 302 can connect to fluid line 301 of a peritoneal dialysis generation system by any means known in the art. For example, the bottom of fluid tube 302 can include a capped and threaded portion that can mate with a threaded portion on a peritoneal dialysis system. Alternatively, the fluid tube 302 can include a rigid connector for connection to the peritoneal dialysis generation system. A flap (not shown in FIGS. 3A-B) can cover the rigid connector prior to connection to separate the contents of the dialysate container 300 from the outside environment. Alternatively, a peelable layer can be placed on the bottom of fluid tube 302 that can be removed prior to connection. The peelable layer can be formed from a polyolefin film or metal foil. The material can be made from any long-lasting, non-reactive material suitable for storage, sterility, and transport. The peelable layer can be made from any of a polymer selected from at least one of LLDPE (Linear Low Density Polyethylene), LDPE (Low Density Polyethylene) and HDPE (High Density Polyethylene), ethylene-vinyl acetate copolymer, ethylene-methyl acrylate copolymer and HDPE or any suitable material. The materials should form a consistent hermetic seal for leak protection and preserve the materials contained inside. The materials should provide tamper-evident protection but be sufficiently easy to open or peel.

The dialysate container 300 can be constructed from a flexible or rigid material, as desired. In certain embodiments, the dialysate container 300 can be made from mono or multilayer film material, including polypropylene-polyethylene or polypropylene-polyethylene-polyamide for multilayer polyolefin-based films; a monolayer polyolefin film such as polypropylene or polyethylene, or vinyl based films such as PVC or EVA. Alternatively, any other suitable material known to those of skill in the art can be used. In general, the materials should be non-reactive to the materials contained inside the dialysate container 300. The dialysate container 300 can be made from a flexible material formed from two pieces where the pouch side 306 can be welded to another pouch side (not shown). The pouches and/or containers can also be semi-flexible, semi-rigid, or rigid. The pouches and/or containers can be fabricated from any suitable process known to those of ordinary skill. One of ordinary skill will understand that the pouch can be made from any suitable material depending on any desired manufacturing, usage, and size constraints.

In addition to, or as an alternative to the venturi system illustrated in FIGS. 3A-B, the system can include other mixing elements that manipulate flow or cause turbulence to mix the incoming water with the solid or highly concentrated liquid material in the dialysate container. In certain embodiments, the mixing element can include one or more of a static mixer, a propeller, a magnetic stirrer, a vibration plate, or any other element or nozzle that can create turbulence at the inlet to facilitate mixing.

One skilled in the art will understand that various combinations and/or modifications and variations can be made in the described systems and methods depending upon the specific needs for operation. Various aspects disclosed herein may be combined in different combinations than the combinations specifically presented in the description and accompanying drawings. Moreover, features illustrated or described as being part of an aspect of the disclosure may be used in the aspect of the disclosure, either alone or in combination, or follow a preferred arrangement of one or more of the described elements. Depending on the example, certain acts or events of any of the processes or methods described herein may be performed in a different sequence, may be added, merged, or left out altogether (e.g., certain described acts or events may not be necessary to carry out the techniques). In addition, while certain aspects of this disclosure are described as performed by a single module or unit for purposes of clarity, the techniques of this disclosure may be performed by a combination of units or modules associated with, for example, a medical device.

What is claimed is:

1. A system, comprising:
   a water source;
   a dialysate container,
      wherein the dialysate container initially contains solid material or a concentrated liquid;
   a recirculation line,
      wherein the recirculation line has an inlet and an outlet fluidly connected to the dialysate container; and
   a control system,
      wherein the control system is programmed to pump a predetermined volume or a predetermined mass of water into the dialysate container to generate a peritoneal dialysis fluid.

2. The system of claim 1, further comprising a water purification module between the water source and the dialysate container.

3. The system of claim 2, wherein the water purification module comprises one or more selected from the group consisting of a sorbent cartridge, activated carbon, a reverse osmosis module, an electrodialysis module, a carbon filter, and a nanofilter.

4. The system of claim 1, further comprising a mixing element in the dialysate container.

5. The system of claim 4, wherein the mixing element comprises a venturi tube in an inlet of the dialysate container.

6. The system of claim 5, the venturi tube comprising:
a first section distal to an interior portion of the dialysate container, the first section having a first diameter,
a second section distal to the first section and proximal to the interior portion of the dialysate container, the second section having a second diameter smaller than the first diameter forming a constriction, and
a third section distal to the second section and extending inwardly into the interior portion of the dialysate container, the third section having a third diameter larger than the second diameter, and having a suction port exposing an interior of the venturi tube to the interior portion of the dialysate container.

7. The system of claim 1, further comprising a cycler fluidly connectable to the dialysate container.

8. The system of claim 7, the control system further programmed to pump a predetermined volume of the peritoneal dialysis fluid into the cycler.

9. The system of claim 7, further comprising a sterilization module between the dialysate container and the cycler.

10. The system of claim 1, wherein the solid material or concentrated liquid comprises sodium chloride, calcium chloride, magnesium chloride, sodium lactate, sodium bicarbonate, and an osmotic agent.

11. The system of claim 10, wherein the osmotic agent is dextrose.

12. The system of claim 1, wherein the water source is a tap water source.

13. The system of claim 1, wherein the water source is a purified water source.

14. The system of claim 1, wherein the dialysate container initially contains the solid material.

15. The system of claim 1, further comprising at least one sensor in communication with the control system, the control system determining a concentration of at least one solute in the peritoneal dialysis fluid based on data from the at least one sensor.

16. The system of claim 1, further comprising at least one heater between the water source and the dialysate container.

17. The system of claim 1, further comprising a heater in the recirculation line.

18. A system, comprising:
a water source;
a dialysate container,
wherein the dialysate container initially contains solid material or a concentrated liquid;
wherein the dialysate container is fluidly connected to an inlet and an outlet of a recirculation line; and
a control system,
wherein the control system is programmed to pump a predetermined volume or a predetermined mass of water into the dialysate container to generate a peritoneal dialysis fluid.

19. The system of claim 18, further comprising a water purification module between the water source and the dialysate container.

20. The system of claim 19, wherein the water purification module comprises at least one of a sorbent cartridge, activated carbon, a reverse osmosis module, an electrodialysis module, a carbon filter, a nanofilter, or any combination thereof.

21. The system of claim 18, further comprising a cycler fluidly connectable to the dialysate container.

22. The system of claim 21, the control system further programmed to pump a predetermined volume of the peritoneal dialysis fluid into the cycler.

23. The system of claim 21, further comprising a sterilization module between the dialysate container and the cycler.

24. The system of claim 18, wherein the solid material or concentrated liquid comprises sodium chloride, calcium chloride, magnesium chloride, sodium lactate, sodium bicarbonate, and an osmotic agent.

25. The system of claim 24, wherein the osmotic agent is dextrose.

26. The system of claim 18, wherein the water source is a tap water source.

27. The system of claim 18, wherein the water source is a purified water.

28. The system of claim 18, further comprising at least one sensor in communication with the control system, the control system determining a concentration of at least one solute in the peritoneal dialysis fluid based on data from the at least one sensor.

29. The system of claim 28, further comprising a heater in the recirculation line.

30. The system of claim 18, further comprising at least one heater between the water source and the dialysate container.

* * * * *